United States Patent [19]

Mann

[11] Patent Number: 5,056,504

[45] Date of Patent: Oct. 15, 1991

[54] INFLATABLE BALL HAND SPLINT

[75] Inventor: Donaerl B. Mann, St. Petersburg, Fla.

[73] Assignee: D'mannco, Inc., Clearwater, Fla.

[21] Appl. No.: 709,591

[22] Filed: Jun. 3, 1991

Related U.S. Application Data

[63] Continuation-in-part of Ser. No. 612,319, Nov. 13, 1990, Pat. No. 5,020,515.

[51] Int. Cl.⁵ ............................ A61H 1/02; A61F 5/04
[52] U.S. Cl. .................... 128/26; 128/87 R; 128/DIG. 20
[58] Field of Search ............... 128/DIG. 20, 25 R, 26, 128/77, 87 R, 878, 879; 273/54 B, 54 R

[56] References Cited

U.S. PATENT DOCUMENTS

| | | | |
|---|---|---|---|
| 3,217,333 | 11/1965 | Sweet | 128/DIG. 20 |
| 3,457,912 | 1/1967 | Clark | 128/26 |
| 3,581,740 | 6/1971 | Sherbourne | 128/26 |
| 3,937,215 | 2/1976 | Barthlome | 128/DIG. 20 |
| 4,173,218 | 11/1979 | Cronin | 128/DIG. 20 |
| 4,182,320 | 1/1980 | Sweeney | 128/DIG. 20 |
| 4,274,399 | 6/1981 | Mummert | 128/DIG. 20 |
| 4,522,197 | 6/1985 | Hasegawa | 128/25 R |
| 4,619,250 | 10/1986 | Hasegawa | 128/25 R |
| 4,671,258 | 6/1987 | Barthlome | 128/25 R |
| 4,706,658 | 11/1987 | Cronin | 128/DIG. 20 |

*Primary Examiner*—Robert A. Hafer
*Assistant Examiner*—Michael Brown
*Attorney, Agent, or Firm*—Herbert W. Larson

[57] ABSTRACT

An inflatable hand splint for treatment of patient with arthritic or stroke paralyzed wrists employs a pliable wrist element attached at a first end to an inflatable ball. The ball has an external air valve for attaching to a hand operated air pump. The second end of the pliable element extends downwardly along the underside of the patient's wrist and is strapped to the patient's forearm with a pair of straps engaged by hook and loop material. A front end of a hard plastic support member is inserted between the fingers and palmer portion of the patient's hand. The rear end of the support member is located below the pliable wrist element and is also strapped to the patient's forearm. The deflated ball is inserted under the patient's finger tips and inflated to move the fingers away from the palmer region.

11 Claims, 2 Drawing Sheets

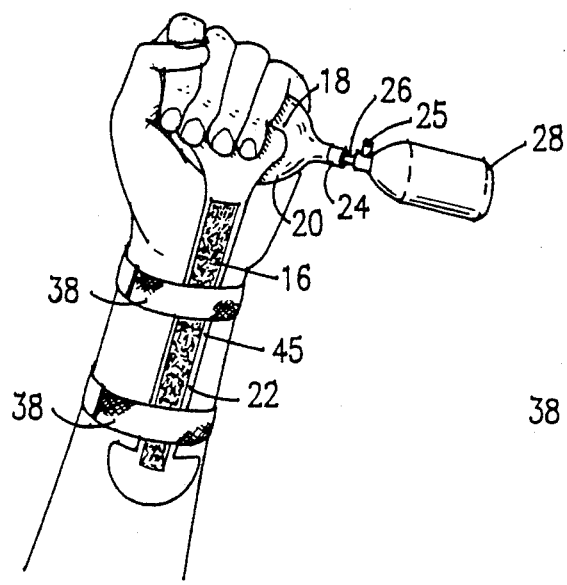
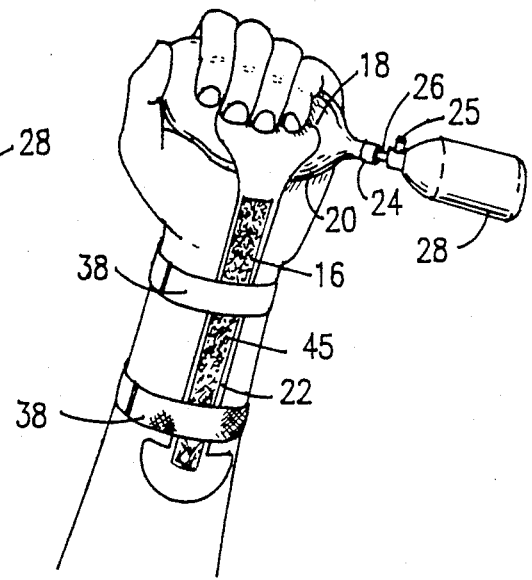
FIG. 1   FIG. 2
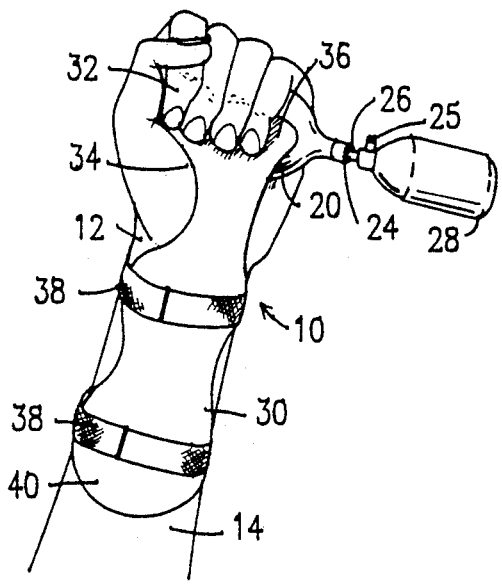
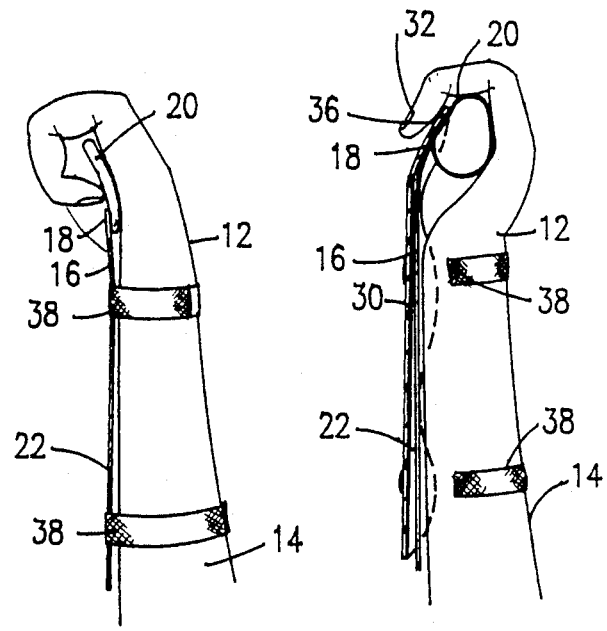
FIG. 3   FIG. 4   FIG. 5

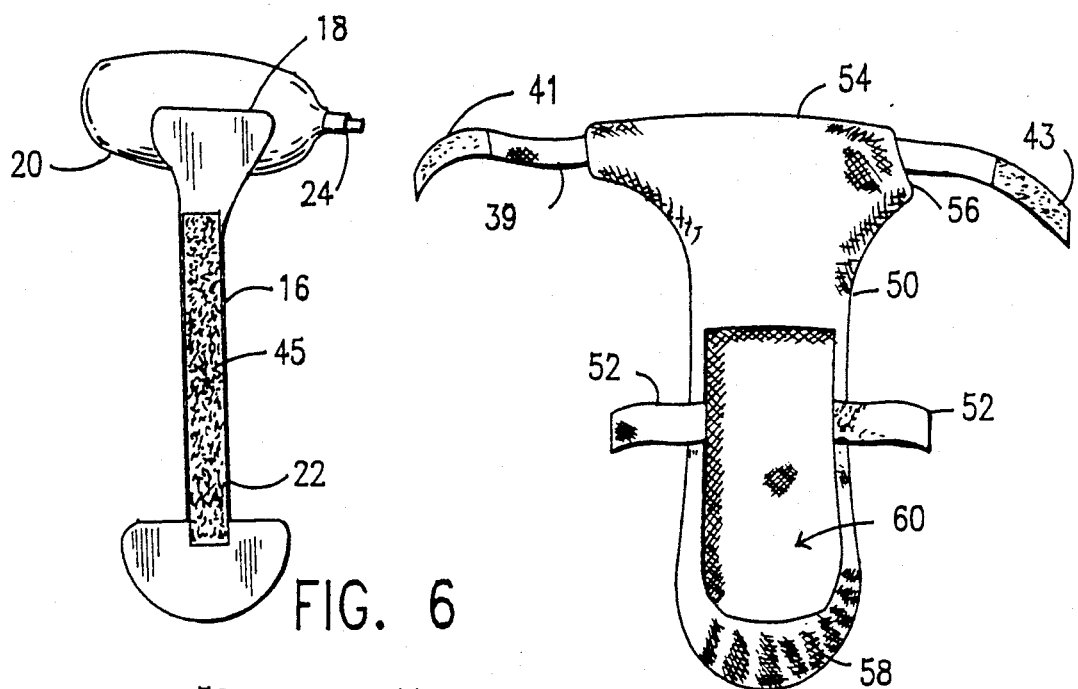
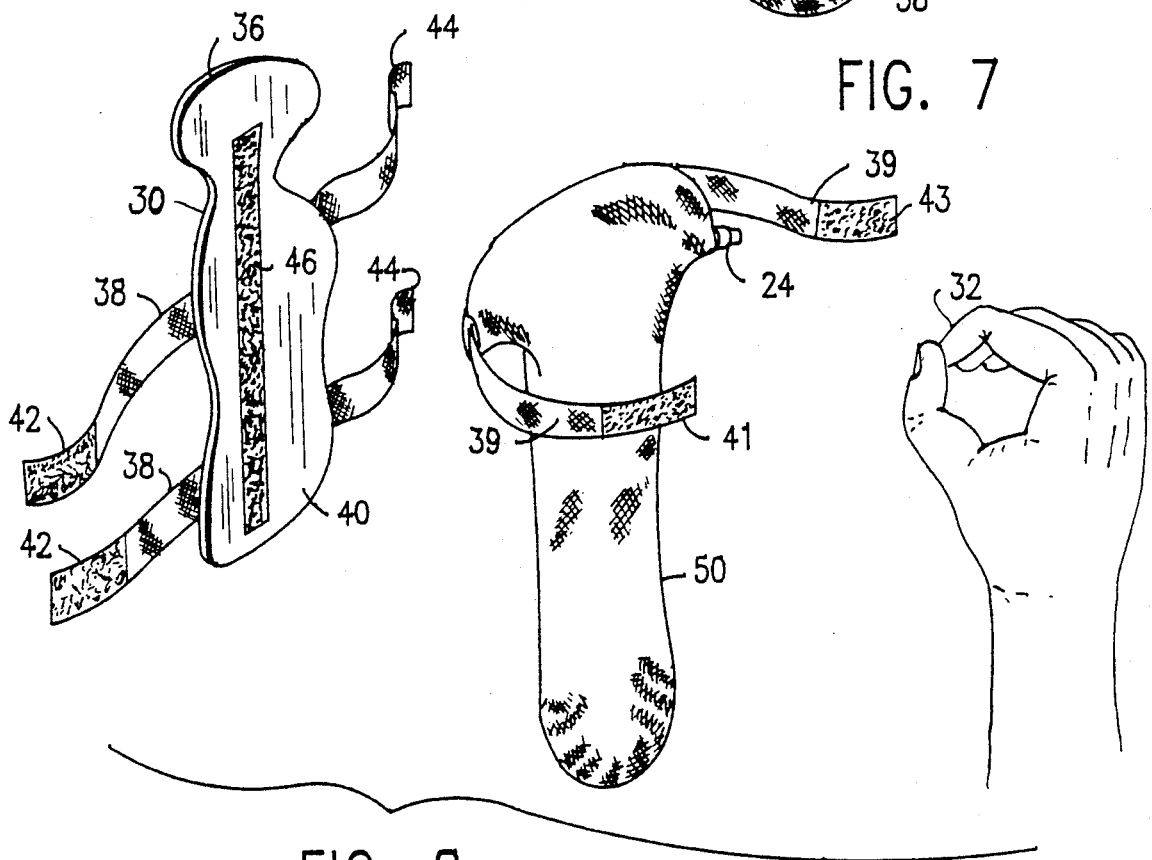

INFLATABLE BALL HAND SPLINT

PRIOR APPLICATION

This Application is a continuation-in-part of my Application Ser. No. 07/612,319, filed Nov. 13, 1990, now U.S. Pat. No. 5,020,515.

BACKGROUND OF THE INVENTION

1. Field of the Invention

This invention relates to hand splints. More particularly, it refers to an inflatable finger straightening device together with a method for use with stroke victims or other persons suffering from hand paralysis to unbend severely contorted fingers.

2. Description of the Prior Art

Hand splints, such as those shown in U.S. Pat. Nos. 3,938,509 and 4,538,600 are used to correct orthotic conditions or paralytic conditions caused by stroke. These corrective splints assist physical therapists in relieving the effects of a paralyzed hand which tends to turn in towards the wrist and prevents the patient from using his or her fingers. Other patents describe devices for exercising a patient's hand such as U.S. Pat. Nos. 3,457,912; 3,581,740; 3,937,215; 4,274,399; 4,522,197; 4,619,250 and 4,671,258. Although the splints set forth in the above indicated patents are effective for treatment of wrist paralyzed patients and to exercise fingers, a problem frequently occurs in trying to move the fingers away from the palmer region of the hand in stroke victims. The fingers tend to dig into the palm and cannot be forced away if left in that position for long periods of time. An improved hand splint is needed for patients with severely paralyzed wrists to exercise fingers in a direction outward from the palmer region of the hand to prevent fixation of the fingers in an unnatural position.

SUMMARY OF THE INVENTION

I have invented an improved inflatable hand splint device for use on arthritic and stroke patients which is easily applied under the patient's fingers between the finger tips and the palmer region of the hand. By inflating my device the fingers are gently moved outward from the palmer region repeatedly on a scheduled basis to prevent fixation of the fingers in a contorted position.

My inflatable hand splint has a pliable soft vinyl ball attached to a pliable wrist element. The ball has an external air valve for attaching to a hand operated air pump. The pliable wrist element extends downwardly along the lower wrist of a patient and is strapped to the patient's wrist with at least two hook and loop wrist bands. A deflated ball is gently slipped between the finger tips and palmer region of the patient. The ball is gently inflated and deflated to exercise the fingers on a regular schedule. When the finger tips have moved away from the palmer region of the hand a first end of a hard plastic support is slipped under the tips of the fingers exterior to an outer side of the pliable wrist element. The wrist straps hold both the hard plastic support and pliable wrist element in place under the wrist and forearm of the patient. The pliable wrist element and the ball can have a soft cotton dress enclosing them to cover the entire length of the hand splint.

BRIEF DESCRIPTION OF THE DRAWINGS

The invention may be best understood by those having ordinary skill in the art by reference to the following detailed description when considered in conjunction with the accompanying drawings in which:

FIG. 1 is a perspective view of a deflated ball attached to a pliable wrist element strapped to a patient's forearm.

FIG. 2 is a perspective view of an inflated ball attached to the pliable wrist element strapped to a patient's forearm.

FIG. 3 is a perspective view of the inflated hand splint with a hard plastic wrist support in place.

FIG. 4 is a left hand left side view of a deflated ball positioned between fingers and palm before insertion of the hard plastic wrist support.

FIG. 5 is a left hand, left side partial section view of an inflated ball and the hard plastic wrist support.

FIG. 6 is a top plan view of the ball attached to the pliable wrist element.

FIG. 7 is a top plan view of a cotton cover for the ball and pliable wrist element.

FIG. 8 is an exploded view of the hard plastic wrist support engaging the cotton dress positioned for attachment to a patient's wrist and containing the ball and pliable wrist element.

DETAILED DESCRIPTION OF THE INVENTION

Throughout the following detailed description, the same reference numerals refer to the same elements in all figures.

The inflatable hand splint 10 shown in FIG. 3 is strapped to the lower wrist portion 12 and forearm 14 of a patient. The inflatable hand splint 10 has a pliable wrist element 16 which has a first end 18 attached to an air bladder or inflatable ball 20 and a second end 22 extending away from the ball 20 along the wrist of the patient. An air valve 24 is integral with the ball 20 and is capable of receiving a tube 26 from a small hand held air pump 28. A release valve 25 on the air pump 28 allows a patient to force air out of the ball 20 by pressing on the ball with fingers 32 and pressing on valve 25. The air pump 28 is usually made from an elastomer or soft plastic. The pliable wrist element 16 seen in FIG. 1 has its first end 18 attached to the deflated ball 20. The attachment can be by glue or electron welding. In FIG. 2 the first end 18 is attached to an inflated ball 20.

The pliable wrist element 16 is made from a pliable vinyl plastic. It should be appreciated that an elastomer or other pliable material may be substituted for the vinyl plastic in element 16.

A hard plastic wrist support 30 as seen in FIGS. 3 and 5 is inserted between fingers 32 and the palmer region 34 of a patient after the fingers 32 are partially moved away from the palmer region 34. Only the first end 36 of the hard plastic 30 is slipped under the fingers. The remainder or second end 40 of hard plastic 30 supports the wrist 12 and forearm 14 of the patient. The pliable plastic wrist support element 16 and hard plastic 30 are strapped to the patient as seen in FIG. 3 with at least two hook and loop straps 38. Strap 39 attached to soft goods 50 holds the pliable wrist element 16 and ball 20 in place over the patient's hand. The straps 38 can be made of cloth or a plastic and have a hook material 42 at one end and a corresponding loop material 44 at a second end for engagement together around the patient's wrist 12 and forearm 14. In like manner, strap 39 can be made of cloth or plastic and has hook material 41 at one end and corresponding loop material 43 at a second end for engagement around a fist of the patient.

The hard plastic 30 can be made of polyethylene, polypropylene, a polyethylene copolymer or other like substance. It also could be made of wood or metal such as stainless steel or aluminum.

The inner surface of the hard plastic 30 can have a strip of hook material 46 glued to the plastic as seen in FIG. 8. This hook material can engage a loop material 45 on the pliable wrist element 16 or engage the cotton dress 50. The cotton dress 50 covering the ball 20 and pliable wrist element 16 is seen in FIG. 7. This dress 50 provides additional comfort to the patient by absorbing sweat. It can be frequently washed and replaced over the pliable element 16 and ball 20. A small hole 56 in the dress 50 allows valve 24 to protrude outwardly. The top portion 54 accommodates ball 20 and the bottom portion 58 accommodates end 22 of the pliable element 16. Hook and loop straps 52 hold the end 22 in place within pocket 60 in dress 50.

After a patient's fingers have been exercised by the inflatable hand splint 10 of this invention so that the fingers do not touch the palmer region 34 any longer, a fabric material, not shown, can be substituted for the inflatable hand splint.

Other like materials can be substituted for the materials set forth above to obtain equivalent results.

Having thus described the invention, what is claimed and desired to be secured by Letters Patent is:

1. An inflatable hand splint comprising
   a pliable wrist element attached at a first end to an inflatable ball and having a second end extending away from the ball, an air valve integral with the ball connectable to a hand operated air pump to provide a source of air to inflate the ball,
   a stiff sheet substantially conforming in width and contour to a patient's wrist and forearm located in parallel alignment with the pliable wrist element, at least two straps each having means to connect together at oppositely connecting ends attached to an exterior surface of the stiff sheet and the pliable wrist element located adjacent an interior surface of the stiff sheet and between the stiff sheet and a wrist and forearm of a patient, the straps being wound around and connected at each end to hold the stiff sheet and pliable wrist element in position around a forearm of a patient,
   the deflated ball attached at the first end of the pliable wrist element being located between contorted fingertips and palmer portion of the hand of the patient and the ball when inflated causing the patient's fingers to move away from the palmer region of the hand.

2. The inflatable hand splint according to claim 1 wherein a soft cloth dress encloses the pliable wrist element and ball.

3. The inflatable hand splint according to claim 1 wherein the connectable strap ends and means to connect together the straps are corresponding hook or loop material at the ends of each strap.

4. The inflatable hand splint according to claim 1 wherein the pliable wrist element and ball are made from a soft polymer.

5. The inflatable hand splint according to claim 4 wherein the pliable wrist element is made from a vinyl polymer and the hard plastic from a polymer is selected from the group consisting of polycarbonate, polyethylene, polypropylene and a copolymer thereof.

6. The inflatable hand splint according t claim 1 wherein the first end of the pliable wrist element is glued to the ball.

7. A method of moving contorted fingers of a stroke patient away from the palmer region of the patient's hand comprising
   inserting a deflated ball, attached to a first end of a pliable wrist element, between the fingertips and palmer region of the patient's hand, with a second end of the pliable element extending along a lower wrist and forearm of the patient, the ball having an attached air valve;
   inserting a stem leading to a hand held air pump into the air valve and alternatingly inflating an deflating the ball to exercise the patient's fingers and move them away from the palmer portion of the patient's hand.

8. The method according to claim 7 wherein a stiff sheet is applied to an outer surface of the pliable wrist element and at least two straps attached to the stiff sheet are wrapped around the patient's forearm to retain the hard sheet and pliable wrist element juxtaposed to an underside of the patient's forearm.

9. A method according to claim 7 wherein a soft absorbent cloth dress is draped around the pliable wrist element and ball.

10. The method according to claim 9 wherein a pair of strap ends integral with opposite side edges of the soft cloth covering the pliable wrist element and ball are tightly wrapped around the patient's fist and held together by hook and loop material.

11. A method according to claim 9 wherein the cloth dress is made from cotton.

* * * * *